United States Patent [19]

Hyman

[11] Patent Number: 5,629,177
[45] Date of Patent: *May 13, 1997

[54] METHOD FOR THE ENZYMATIC SYNTHESIS OF OLIGONUCLEOTIDES USING THERMOSTABLE 3'-PHOSPHATASE

[76] Inventor: Edward D. Hyman, 2100 Sawmill Rd., River Ridge, La. 70123

[*] Notice: The portion of the term of this patent subsequent to Dec. 23, 2012, has been disclaimed.

[21] Appl. No.: 259,308

[22] Filed: Jun. 13, 1994

Related U.S. Application Data

[63] Continuation-in-part of PCT/US93/12456, Dec. 21, 1993, which is a continuation-in-part of Ser. No. 161,224, Dec. 2, 1993, which is a continuation-in-part of Ser. No. 100,671, Jul. 30, 1993, which is a continuation-in-part of Ser. No. 995,791, Dec. 23, 1992, Pat. No. 5,436,143.

[51] Int. Cl.$^6$ .................... C12P 19/34; C12Q 1/68; C07H 21/04; C07H 21/00
[52] U.S. Cl. .................... 435/91.2; 435/91.1; 435/6; 536/25.3; 536/25.6
[58] Field of Search ............ 435/91, 6; 536/25.3, 536/25.6; 935/16

[56] References Cited

U.S. PATENT DOCUMENTS

| | | | |
|---|---|---|---|
| 3,850,749 | 11/1974 | Kaufmann et al. | 435/91.3 |
| 4,661,450 | 4/1987 | Kempe et al. | 435/91.4 |
| 4,962,020 | 10/1990 | Tabor et al. | 435/6 |
| 4,987,071 | 1/1991 | Cech et al. | 435/91.35 |
| 5,242,817 | 9/1993 | Kelly et al. | 435/220 |
| 5,256,549 | 10/1993 | Urdea et al. | 435/91 |
| 5,409,811 | 4/1995 | Tabor et al. | 435/6 |
| 5,436,143 | 7/1995 | Hyman | 435/172.3 |

FOREIGN PATENT DOCUMENTS

| | | |
|---|---|---|
| 0196101 | 10/1986 | European Pat. Off. . |
| 2169605 | 7/1986 | United Kingdom . |

OTHER PUBLICATIONS

Shum et al., "Simplified method for large scale enzymatic synthesis of oligoribonucleotides", Nucleic Acids Res. 5: 2297–2311 (1978).
Schott et al., "Single-step elogation of oligodeoxynucleotides using terminal deoxynucleotidyl transferase", Eur. J. Biochem. 143: 613–620 (1984).
Mackey et al., "New approach to the synthesis of polyribonucleotides of defined sequence", Nature 233: 551–553 (1971).
Hinton et al., "The preparative synthesis of oligodeoxy–ribonucleotides using RNA ligase", Nucleic Acids Res. 10: 1877–1894 (1982).
England et al., "Dinucloetide pyrophosphates are substrates for T4–induced RNA ligase", Proc. Nat'l Acad Sci. (USA) 74: 4839–4842 (1977).
Beckett et al., "Enzymatic Synthesis of Oligoribonucleotides", in *Oligonucleotide Synthesis: A Practical Approach*, M.J. Gait ed., pp. 185–197 (1984).

Mudrakovskaya et al., "RNA Ligase of Bacteriophage T4. VII: A solid pahse enymatic synthesis of oligoribonucelotides", Biorg. Khim. 17: 819–822 (1991).
Stuart et al., "Synthesis and Properties of Oligodeoxynucleotides with an AP site at a preselected location", Nucleic Acids Res. 15: 7451–7462 (1987).
Norton et al., "A ribonuclease specific for 2'–O–Methyltaed Ribonucleic Acid", J. Biol. Chem. 242: 2029–2034 (1967).
Eckstein et al., "Phosphorothioates in molecular biology", TIBS 14:97–100 (1989).
Bryant et al., "Phosphorothioate Substrates for T4 RNA Ligase", Biochemistry 21: 5877–5885 (1982).
McLaughlin et al., "Donor Activation in the T4 RNA Ligase Reaction", Biochemistry 24: 267–273 (1985).
Ohtsuka et al., "A new method for 3'–labelling of polyribonucleotides by phosphorylation with RNA ligase and its aplication to the 3'–modification for joining reactions", Nucleic Acids Res. 6: 443–454 (1979).
Kornberg, A., "Reversible Enzymatic Synsnthesis of Diphosphopyridine nucleotide and inorganic pyrophosphate", J Biol. Chem. 182: 779–793 (1950).
Kaplan et al., "Enzymatic Deamination of Adenosine Derivatives", J. Biol. Chem. 194: 579–591 (1952).
Bartkiewicz et al., "Nucleotide pyrophosphatase from potato tubers", Eur. J. Biochem. 143: 419–426 (1984).
Rand et al., "Sequence and cloning of bacteriophage T4 gene 63 encoding RNA ligase and tail fibre attachment activities", The EMBO Journal 3: 397–402 (1984).
Heaphy et al., "Effect of Single Amino Acid Chnages in the Region of the Adenylation Site of T4 RNA llgase", Biochemistry 26: 1688–1696 (1987).
Lowe et al., "Molecular cloning and expression of a cDNA encoding the membrane–associated rat intestinal alkaline phosphatase", Biochem. Biophys. Acta 1037: 170–177 (1990).
Razzell et al., "Studies on POlynucleotides: III. Enzymatic Degaradtion. Substrate Specificity and Properties of Snake Venom Phosphodiesterase", J. Biol. Chem. 234: 2105–2113 (1959).
Tessier et al., "Ligation of Single–Stranded Oligodeoxyribonucleotides by T4 RNA Ligase", Analytical Biochemistry 158: 171–178 (1986).
England et al., "Enzymatic Oligoribonucleotide Synthesis with T4 RNA Ligase", Biochemistry 17: 2069–2076 (1978).
Uhlenbeck et al. "T4 RNA Ligase", The Enzymes XV: 31–58 (1982).

(List continued on next page.)

*Primary Examiner*—Stephanie W. Zitomer
*Assistant Examiner*—Dianne Rees
*Attorney, Agent, or Firm*—Oppedahl & Larson

[57] ABSTRACT

An oligonucleotide is synthesized by adding a 3'-phosphate blocked nucleotide to a primer, removing the blocking group from the primer-blocked nucleotide product using a thermostable 3'-phosphatase enzyme, and repeating these steps until the desired nucleotides have been added to the primer. A suitable phosphatase enzyme for use in this method is a thermostable phosphatase derived from the hyperthermophilic archaebacterium *Pyrococcus furiosus*.

24 Claims, No Drawings

OTHER PUBLICATIONS

Hoffman et al. "Synthesis of reactivity of intermediates formed in the T4 RNA ligase reaction", Nucleic Acids Res. 15: 5289–5301 (1987).

Middleton et al., "Synthesis and Purification of Olignucleotides Using T4 RNA Ligase and Reverse Phase Chromatography", Analytical Biochemistry 144: 110–117 (1985).

Soltis et al., "Independent Locations of Kinase and 3'-Phosphatase Activities on T4 Polynucleotide Kinase", J. Biol. Chem. 257: 11340–11345 (1982).

Apostol et al., "Deletion Analysis of a Multifunctional Yeast tRNA Ligase Polypeptide", J. Biol. Chem. 266: 7445–7455 (1991).

Becker et al., "The Enzymatic Clevage of Phosphate Termini from Polynucleotides", J. Biol. Chem. 242: 936–950 (1967).

Greer et al., "RNA Ligase in Bacteria: Formation of a 2', 5'Linkage by an *E. coli* Extract", Cell 33: 899–906 (1983).

Beabealashvilli et al., "Nucleoside 5'–triphosphates modified at sugar residues as substrates for calf thymus terminal deoxynuceltoidyl transferase and for AMV reverse transcriptase", Biochim. Biophys. Acta 868: 135–144 (1986).

Schwartz et al., "Enzymatic Mechanism of RNA LIgase from Wheat Germ", J. Biol. Chem. 258: 8364–8383 (1983).

Lehman et al., "The Deoxyribonucleases of *Escherichia coli*", J. Biol. Chem. 239: 2628–2636 (1964).

Itakura et al., "Syntethis and Use of Synthetic Oligonucleotides", Ann. Rev. Biochem. 33: 323–356 (1984).

Sambrook et al., Molecular Cloning: A Laboratory Manual, pp. 7.40–7.41, Cold Spring Harbor Press, Cold Spring Harborm NY (1989).

Nieuwlandt et al., "In vivo porcessing of an intron–containing archael t–RNA", Molecular Microbiology 8: 93–99 (1993).

Sambrook et al., In Molecular Cloning a Laboratory Manuel, Cold Spriong Harbor, 1989, pp. 5.6 and 5.72).

Dolapchiev, Biochimica and Biophysica Acta, 667:355–360, 1981.

Shum et al. Nar 5:2297–2309, 1978.

Uhlenbeck the Enzymes xv:31,58, 1982.

METHOD FOR THE ENZYMATIC SYNTHESIS OF OLIGONUCLEOTIDES USING THERMOSTABLE 3'-PHOSPHATASE

This application is a continuation-in-part of International Patent Application PCT/US93/12456 filed Dec. 21, 1993 designating the United States now U.S. patent application Ser. No. 08/464,778, which is a continuation-in-part of copending U.S. patent application Ser. No. 08/161,224 filed Dec. 2, 1993, which is a continuation-in-part of copending U.S. patent application Ser. No. 08/100,671 filed Jul. 30, 1993, which is a continuation-in-part of U.S. patent application 07/995,791 filed Dec. 23, 1992 now U.S. Pat. No. 5,436,143 issued Jul. 25, 1995, all of which are incorporated herein by reference.

BACKGROUND OF THE INVENTION

Synthetic oligonucleotides play a pivotal role in molecular biology research, useful especially for DNA sequencing, DNA amplification, and hybridization. Novel methods for the synthesis of oligonucleotides have been described previously by the inventor in International Application PCT/US93/12456 and in U.S. patent applications 08/161,224, 08/100,671, and 07/995,791 to replace both the obsolete enzymatic methods and the current chemical methods. These methods, referred to herein collectively as the "One Pot" method basically involve repeated cycles of extending an oligonucleotide primer using a nucleotide substrate having a 3'-blocking group, thus forming an extended primer with a blocking group at its 3'-end; and removal of the 3'-blocking group from the extended primer to prepare the extended primer for the addition of the next nucleotide. When the defined sequence calls for the same nucleotide to be incorporated more than once in succession, unreacted blocked nucleotide may be reused in the subsequent cycle (s). In this case, the blocking group is selectively removed from the primer-blocked nucleotide product substantially without deblocking of the unreacted blocked nucleotide. Otherwise, the method includes the further step of converting any unreacted blocked nucleotide to an unreactive form which is substantially less active as a substrate for the chain extending enzyme than the blocked nucleotide. The ease with which this method can be automated will foster a new generation of oligonucleotide synthesizers with enormous throughput, increased reliability, lower cost per synthesis, and with environmentally friendly reagents.

One of the major costs associated with the enzymatic synthesis involving repetitive cycles is the cost of replenishing the enzymes for each cycle. To reduce this cost, the inventor has previously proposed that the use of a thermostable enzymes would obviate the need for replenishment after each cycle of the method.

All of the five major enzymes of the One Pot method—RNA Ligase, AMP Degrading Enzyme, Exonuclease (e.g. Phosphodiesterase I), Alkaline Phosphatase, and 3'-Phosphatase—may be used in the One Pot method as thermostable versions, provided that "significant" co-incubation of enzyme activities which could be deleterious to the synthesis is avoided. Significant co-incubation is defined by the user in terms of the desire for a certain level of product purity or product yield.

It is an object of the present invention to provide an improvement of the One Pot method in which a thermostable 3'-Phosphatase is employed.

It is a further object of the present invention to provide an improved method for synthesizing an oligonucleotide by employing a thermostable 3'-Phosphatase isolated from the hyperthermophilic archaebacterium *Pyrococcus furiosus*.

SUMMARY OF THE INVENTION

In accordance with the invention, there is provided a method for enzymatic synthesis of a region of an oligonucleotide having a defined sequence. The method involves the steps of:

(a) combining an oligonucleotide primer and a blocked nucleotide, or a blocked nucleotide precursor that forms a blocked nucleotide in situ, in a reaction mixture in the presence of RNA Ligase, such that a primer-blocked nucleotide product is formed, wherein the blocked nucleotide substrate comprises a nucleotide to be added to form part of the defined sequence and a 3-phosphate blocking group attached to the nucleotide effective to prevent the addition of more than one blocked nucleotide to the primer;

(b) removing the blocking group from the 3' end of the primer-blocked nucleotide product using a thermostable 3-Phosphatase to form a primer-nucleotide product and one or more non-products, said non-products derived from the oligonucleotide primer or the blocked nucleotide substrate; and (c) repeating a cycle of steps (a) and (b) using the primer-nucleotide product from step (b) as the oligonucleotide primer of step (a) of the next cycle, without prior separation of the primer-nucleotide product from any non-product and without prior inactivation of 3-Phosphatase.

A suitable phosphatase enzyme for use in this method is a thermostable phosphatase derived from the hyperthermophilic archaebacterium *Pyrococcus furiosus*. This enzyme is not inactivated by the heating step(s) of the method, and therefore does not require replenishment for the subsequent cycle(s). Synthesis of an oligonucleotide region is accomplished by adding 3'-Phosphatase in the first cycle.

DETAILED DESCRIPTION OF THE INVENTION

The One Pot Enzymatic method for the synthesis of oligonucleotides has been improved by the use of a thermostable 3'-Phosphatase. Thermostable enzymes improve the speed and efficiency of the One Pot method, reduce the consumption of enzyme, reduce the cost per base of oligonucleotide synthesis, and simplify robotic automation of the synthetic method. The general advantages of using thermostable enzymes in the One Pot method include:

(1) The enzyme needs to be added only once to the synthesis reaction, simplifying robotic automation of the method and lowering the cost of the method by reducing enzyme consumption.

(2) Thermostable enzymes are generally active only at high temperatures. Lowering the temperature has the effect of turning off the enzyme activity. This property may be exploited to avoid deleterious co-incubation of enzyme activities. Enzyme activity is turned back on by elevating the temperature.

(3) Thermostable enzymes are generally active at high ionic strengths, which is an advantageous property since salt products, such as potassium phosphate, may build to high levels in a synthesis. High salt concentrations may be useful at high primer concentrations, in order to prevent precipitation of enzyme-oligonucleotide complexes.

(4) Enzymatic reactions are performed at higher temperature, reducing the chance that secondary structure of the primer can form to impair the enzymatic reaction.

(5) Thermostable enzymes generally have enhanced stability and maintain their activity in the presence of organic solvents and chaotropic salts, such as guanidine, urea, and detergents. Such agents may be useful in preventing an undesirable primer secondary structure.

(6) Accumulation of insoluble protein debris, derived from heat inactivation of thermolabile enzymes, is reduced, since thermostable enzymes are not inactivated by heat.

(7) Thermostable enzymes can be maintained for longer periods at room temperature without substantial loss of activity, obviating the need for bulky refrigeration in an automated instrument.

(8) Large scale production of thermostable enzymes in suitable purity is easier than producing thermolabile enzymes. Production is usually performed by cloning the gene coding for the enzyme in an expression vector of a host which normally grows at 37° C. or lower, such as E. coli or yeast. Significant purification of the thermostable enzyme is usually accomplished by heating the extract, thereby denaturing host proteins and leaving the thermostable enzyme intact.

Thermophilic microbes are a common source of thermostable enzymes. Most of the members of the thermophilic microbe family are archaebacteria. In fact, many archaebacteria can grow at temperatures of 100° C. or greater. Several reports exist in the literature of the presence of introns in tRNA molecules; it is likely that all archaebacteria have intron tRNA (Nieuwlandt et al, *Molecular Microbiology*, (1993), 8(1), 93-9). The natural function of the Transfer RNA Ligase holoenzyme is to convert intron-containing tRNA molecules to intron-less mature tRNA. 3'-Phosphatase is one of the three enzyme sub-components of the Transfer RNA Ligase holoenzyme; the other two enzyme sub-components are RNA Ligase and Polynucleotide Kinase. The hyperthermophilic archaebacterium *Pyrococcus furiosus* (Pfu) was found by the inventor to contain a 3'-Phosphatase enzyme, which is useful in the One Pot method for synthesizing oligonucleotides.

The Pfu 3'-Phosphatase preparation used in the synthesis experiments was partially purified from Pfu extracts, as described in example 1. This preparation also contained polynucleotide kinase activity (ATP+ApA), and may also have RNA Ligase activity (ApApC+AppAp). However, since the 3'-Phosphatase activity was observed to be kinetically much faster than the potential RNA Ligase activity, no significant co-incubation was observed for the purpose of demonstrating the workability of the present invention. It is not known if these three activities are present on a single polypeptide.

While a relatively crude preparation of the 3'-phosphatase is useful in the invention, persons skilled in the art will appreciate that more highly purified preparations, particularly to reduce high KCl concentration or interference by non-phosphatase Pfu proteins; or enzymes derived from a recombinant source will further enhance the yield of product obtainable using the method of the invention. In particular, a recombinant enzyme might be constructed to be devoid of 5'-kinase and RNA Ligase activities, particularly if they exist as separate peptide subunits as in bacteriophage T4.

The substrate specificity of partially purified Pfu 3'-Phosphatase was studied. The enzyme efficiently dephosphorylates ApUp and other 3'-phosphate oligonucleotides; the enzyme dephosphorylates very poorly, if at all, 3',5'-ADP and AppAp, although higher enzyme concentrations may be needed to dephosphorylate these substrates. The enzyme is capable of dephosphorylating deoxyribose terminating 3'-phosphates, such as ApApCpdAp, though the rate is roughly ten fold slower. These properties are similar to the bacteriophage T4 3'-Phosphatase. Thus, the enzyme can allow for the reuse of nucleotide substrate AppAp in subsequent cycles for synthesizing repeat regions; and the enzyme is able to deblock extended primers with deoxyribose or ribose 3' ends. One unique property of the enzyme is that it has excellent activity at 74° C., and poor activity at 37° C. and lower. Thus, by lowering the temperature from 74 degrees to 37 degrees, the enzyme activity can be switched off. This property is useful in avoiding co-incubation with RNA Ligase. The enzyme is likely active at 100° C., since *Pyrococcus furiosus* normally grows at 100° C. Inactivation of Pfu 3'-Phosphatase is probably best achieved by proteolytic digestion.

A thermostable Pfu RNA Ligase would also be a useful enzyme in the One Pot method for synthesizing oligonucleotides, provided that Pfu 3'-Phosphatase activity can be removed. It is unknown whether Pfu RNA Ligase is present on a separate polypeptide from 3'-Phosphatase, as in the T4 system; or whether Pfu RNA Ligase is covalently attached to 3'-Phosphatase, as in the yeast system. In the former case, RNA Ligase can be removed chromatographically; in the latter case, RNA Ligase activity can be removed by selective genetic deletion.

Thermostable 3'-phosphatase is useful in all of the various embodiments of the One-Pot method which have been previously described by the inventor. In general, these methods involve the synthesis of a region of an oligonucleotide of defined structure using a chain extending enzyme such as RNA Ligase. First, an oligonucleotide primer and a blocked nucleotide, or a blocked nucleotide precursor that forms a blocked nucleotide in situ, are combined in a reaction mixture in the presence of the chain extending enzyme, such that a primer-blocked nucleotide product is formed. The blocked nucleotide substrate comprises a nucleotide to be added to form part of the defined sequence and a 3'-phosphate blocking group attached to the nucleotide which is effective to prevent the addition of more than one blocked nucleotide to the primer. The second step of the process involves removal of the blocking group from the 3' end of the primer-blocked nucleotide product using a thermostable 3'-Phosphatase to form a primer-nucleotide product. This primer-nucleotide product is then used as the primer in one or more successive cycles of these steps without prior separation of the primer-nucleotide product from any unused reactants or reaction by-products which may be present and without prior inactivation of 3'-Phosphatase.

When the defined sequence being synthesized calls for the same nucleotide to be incorporated more than once in succession, unreacted blocked nucleotide may be reused in the subsequent cycle(s). In this case, the blocking group is selectively removed from the primer-blocked nucleotide product substantially without deblocking of the unreacted blocked nucleotide. In an embodiment of the invention of this type, a single cycle comprises the steps in sequence:

(a) incubation of an oligonucleotide primer with RNA Ligase and AppNp, wherein App is an adenosine diphosphate moiety, and Np is a 3'-phosphate-blocked nucleoside moiety, to form a primer-pNp product; and (b) incubation with a 3'-Phosphatase to form a primer-pN product. The selectivity of the enzymatic dephosphorylation reaction can be controlled by adjusting the amount of enzyme activity present, such that unreacted AppNp is substantially left intact for reuse in the subsequent cycle.

When the defined sequence calls for the addition of different nucleotides, the method includes the further step of converting any unreacted blocked nucleotide to an unreactive form which is substantially less active as a substrate for RNA Ligase than the blocked nucleotide. In this case, higher levels of 3'-phosphatase activity may be employed, or alternative enzymes such as a Dinucleotide Pyrophosphate Degrading enzyme can be used to convert unreacted blocked nucleotide to an unreactive form. For example, in accordance with a preferred embodiment, a single cycle of the method comprises the steps in sequence of:

(a) incubation of an oligonucleotide primer with RNA Ligase and AppNp to form a primer-pNp product;

(b) incubation with an Exonuclease and a Nucleotide Pyrophosphatase (e.g. phosphodiesterase I);

(c) heat inactivation of the Exonuclease and Nucleotide Pyrophosphatase; and (d) incubation with a 3'-Phosphatase. The subsequent cycle is performed by adding new nucleotide substrate, but the addition of more 3'-phosphatase can be avoided because it is not inactivated during the heat inactivation of the other enzymes.

The method will now be further described by way of the following, non-limiting examples.

EXAMPLE 1

Preparation of *Pyrococcus furiosus* 3-Phosphatase *Pyrococcus furiosus* (Pfu) cell paste was purchased from the Department of Biochemistry at the University of Georgia care of Michael Adams. Approximately 100 g Pfu cell paste was suspended in 500 ml Tris-Cl, pH 8.0, 10 mM EDTA, 10 mM NaCl, 10 mM mercaptoethanol, 0.5% Triton X-100, 0.5 mM phenylmethyl sulfonyl fluoride. Cells were lysed by adding about 20 mg egg white lysozyme and incubating at room temperature for about 30 minutes. The volume of the lysate was doubled by adding 500 ml Tris-Cl, pH 8.0, 10 mM EDTA, 10 mM NaCl, 10 mM mercaptoethanol, 0.5% Triton X-100. Proteins and nucleic acids and protein/nucleic acid complexes were precipitated by slowly adding 50 ml 5% polyethylene imine, pH 7.6. The precipitate was pelleted with difficulty for about 2 hours at 10,000 rpm in a Beckman JA-10 rotor. The precipitate was resuspended in 500 ml 50 mM Tris-Cl, pH 8.0, 20% $(NH_4)_2SO_4$ using a blender at low speed, and pelleted at 9000 rpm in a JA-10 rotor. The supernatant of about 634 ml was transferred to a new vessel and 239 g $(NH_4)_2SO_4$ was added to increase the concentration to 70% saturation to precipitate the protein. The precipitated solution was centrifuged at 9000 rpm in a JA-10 rotor for 2 hours, and the pellet was dissolved in 500 ml 50 mM Tris-Cl, pH 8.0, 1 mM EDTA, 10 mM DTT, 20 um phenylmethyl sulfonyl flouride. The solution was centrifuged at 9000 rpm in a JA-10 rotor for 2 hours to remove insoluble debris to yield a crude extract preparation.

To 200 ml crude extract was added 28.4 g $(NH_4)_2SO_4$ to give a final concentration of about 1.0 Molar. Approximately 80 ml phenyl-sepharose Fast Flow (Pharmacia, Inc.), pre-equilibrated in 20 mM Tris-Cl, pH 8.0, 1.0 M $(NH_4)_2SO_4$, was added to this extract and incubated with occasional shaking for about 15 minutes at room temperature to allow protein binding to the support. The support was recovered by centrifugation at 1500 rpm in a JA-10 rotor for 5 minutes, washed with 400 ml 20 mM Tris-Cl, pH 8.0, 1.0 M $(NH_4)_2SO_4$, and recovered by another centrifugation. The phenyl-sepharose was placed in a column and chromatographed with a linear gradient from 1.0 Molar to 0 Molar $(NH_4)_2SO_4$ in 20 mM Tris-Cl, pH 8.0. Fractions were assayed for 3'-Phosphatase activity with ApUp (Sigma) as a substrate and 3,5-ADP (Sigma) as a control non-substrate. Activity was found in the last fractions. Additional enzyme was eluted using 20 mM Tris-Cl, pH 8.0 containing 20% ethanol.

Active fractions were pumped on an 80 ml Poros 50 HQ column (Perseptive Biosystems, Inc.). Chromatography was performed in 20 mM Tris-Cl, pH 8.0 using a linear gradient of 0 to 0.5 Molar KCl. Active fractions were pooled and concentrated using Centriprep-10 centrifugal ultrafiltration (Amicon). This concentrated fraction served as the source of 3-Phosphatase for the remaining examples. The activity of 3-Phosphatase was such that when diluted four fold, it would dephosphorylate about 80% of the substrate ApUp at 74° C. Subsequent work demonstrated superior purification by using Macroprep methyl HIC support, instead of phenyl-sepharose, obtained from Bioral Inc.

EXAMPLE 2

Synthesis of ApApCpApA with Substrate Reuse

The following solution was placed in a total volume of 23 ul in a tube: 50 Mm Tris-Cl, pH 8.0, 10 mM $MgCl_2$, 10 mM DTT, 0.1% Triton X-100, 0.5 mM ApApC primer, and 4 mM AppAp. AppAp was synthesized enzymatically as previously described by the inventor. The following procedure was performed, with small aliquots removed intermittently for analysis:
Cycle 1
(a) Add 2 ul T4 RNA Ligase (New England Biolabs, 20 units/ul), incubate at 37° C. for 30 minutes, add 50 ul light mineral oil to prevent evaporation, heat at 74° C. for a few minutes.
(b) Add 7 ul Pfu 3-Phosphatase preparation (from example 1), incubate at 74° C. for 2 hours, cool to room temperature.
Cycle 2
(a) Add 2 ul T4 RNA Ligase, incubate at 37° C. for 30 minutes. No AppAp substrate was added.
(b) Heat at 74° C. for 2 hours, cool to room temperature.

The oligonucleotide product was purified by removing the light mineral oil overlay, adding 75 ul 10 mM Tris-Cl, 1 mM EDTA, pH 8.0 and 100 ul 1:1 phenol:$CHCl_3$ containing 0.05% 8-hydroxyquinolone, vortexing, heating at 74° C. for a few minutes, pelleting briefly, and transferring the aqueous supernatant to a new tube. The extraction procedure was repeated with an additional 100 ul 1:1 phenol:$CHCl_3$ containing 0.05% 8-hydroxyquinolone. The extraction effectively removed most of the Pfu proteins. The product sample was analyzed by mass spectroscopy. Product formation was confirmed by the presence of a peak at 1561 daltons.

EXAMPLE 3

Synthesis of ApApCpApA with Substrate Inactivation

The following solution was placed in a total volume of 18 ul in a tube: 50 mM Tris-Cl, pH 8.0, 10 mM $MgCl_2$, 10 mM DTT, 0.1% Triton X-100, 1.5 mM ApApC primer, and 4 mM AppAp. AppAp was synthesized enzymatically as previously described by the inventor. The following procedure was performed, with small aliquots removed intermittently for analysis:
Cycle 1
(a) Add 2 ul T4 RNA Ligase (New England Biolabs, 20 units/ul), incubate at 37° C. for 1 hour.
(b) Add 1 ul Phosphodiesterase I (US Biochemicals, 0.1 unit/ul, also called Nucleotide Pyrophosphatase), incubate at 37° C. for 15 minutes, add 50 ul light mineral oil to prevent evaporation, heat at 72° C. for one minute.

(c) Add 5 ul Pfu 3-Phosphatase preparation (from example 1), incubate at 72° C. for 2 hours, cool to room temperature.

Cycle 2

(a) Add 2 ul T4 RNA Ligase +10 ul 5 mM AppAp, incubate at 37° C. for 1 hour.

(b) Add 1 ul Phosphodiesterase I, incubate at 37° C. for 15 minutes.

(c) Heat at 72° C. for 2 hours, cool to room temperature.

The oligonucleotide product was purified in the same manner as described in example 2. The product sample was analyzed by mass spectroscopy. Product formation was confirmed by the presence of a peak at 1561 daltons.

I claim:

1. A method for synthesizing a portion of an oligonucleotide of defined sequence, comprising the steps of:

(a) combining an oligonucleotide primer and a blocked nucleotide, or a blocked nucleotide precursor that forms a blocked nucleotide substrate in situ, in a reaction mixture in the presence of RNA Ligase, such that a primer-blocked nucleotide product is formed, wherein the blocked substrate comprises a nucleotide to be added to form part of the defined sequence and a 3'-phosphate blocking group attached to the nucleotide effective to prevent the addition of more than one blocked substrate to the oligonucleotide primer;

(b) removing the blocking group from the 3' end of the primer-blocked nucleotide product using a thermostable 3'-Phosphatase to form a primer-nucleotide product; and (c) repeating a cycle of steps (a) and (b) using the primer-nucleotide product from step (b) as the oligonucleotide primer of step (a) of the next cycle, without prior purification of the primer-nucleotide product from the reaction mixture.

2. A method according to claim 1, wherein step (c) is performed without replenishment of 3'-Phosphatase.

3. A method according to claim 2, wherein the 3'-Phosphatase is derived from a thermophilic archaebacterium.

4. A method according to claim 3, wherein the archaebacterium is *Pyrococcus furiosus*.

5. A method according to claim 2, wherein the blocked substrate is AppNp, where N represents a nucleoside or nucleoside analog, such that RNA Ligase can couple the AppNp to the oligonucleotide primer and such that primer-pN product is able to serve as the primer in the next cycle.

6. A method according to claim 5, wherein the 3'-Phosphatase is derived from a thermophilic archaebacterium.

7. A method according to claim 6, wherein the archaebacterium is *Pyrococcus furiosus*.

8. A method according to claim 5, wherein step (c) is performed without replenishment of the blocked substrate.

9. A method according to claim 8, wherein the 3'-Phosphatase is derived from a thermophilic archaebacterium.

10. A method according to claim 9, wherein the archaebacterium is *Pyrococcus furiosus*.

11. A method according to claim 5 further comprising the step of inactivating unreacted blocked nucleotide in the reaction mixture using a Dinucleotide Pyrophosphate Degrading Enzyme prior to step (c) to render it less reactive as a substrate for the chain extending enzyme.

12. A method according to claim 11, wherein the Dinucleotide Pyrophosphate Degrading Enzyme is Nucleotide Pyrophosphatase.

13. A method according to claim 12, wherein the Nucleotide Pyrophosphatase is derived from snake venom.

14. A method according to claim 1, wherein the 3'-Phosphatase is derived from a thermophilic archaebacterium.

15. A method according to claim 14, wherein the archaebacterium is *Pyrococcus furiosus*.

16. A method according to claim 1, wherein the blocked substrate is AppNp, where N represents a nucleoside or nucleoside analog, such that RNA Ligase can couple the AppNp to the oligonucleotide primer and such that primer-pN product is able to serve as the primer in the next cycle.

17. A method according to claim 16, wherein the 3'-Phosphatase is derived from a thermophilic archaebacterium.

18. A method according to claim 17, wherein the archaebacterium is *Pyrococcus furiosus*.

19. A method according to claim 16, wherein step (c) is performed without replenishment of the blocked substrate.

20. A method according to claim 19, wherein the 3'-Phosphatase is derived from a thermophilic archaebacterium.

21. A method according to claim 20, wherein the archaebacterium is *Pyrococcus furiosus*.

22. A method according to claim 16, further comprising the step of inactivating unreacted blocked nucleotide in the reaction mixture using a Dinucleotide Pyrophosphate Degrading Enzyme prior to step (c) to render it substantially less reactive as a substrate for the chain extending enzyme.

23. A method according to claim 22, wherein the Dinucleotide Pyrophosphate Degrading Enzyme is Nucleotide Pyrophosphatase.

24. A method according to claim 23, wherein the Nucleotide Pyrophosphatase is derived from snake venom.

* * * * *